(12) United States Patent
Spallek et al.

(10) Patent No.: US 10,370,163 B2
(45) Date of Patent: Aug. 6, 2019

(54) CONTAINER

(71) Applicant: KOCHER-PLASTIK MASCHINENBAU GMBH, Sulzbach-Laufen (DE)

(72) Inventors: Michael Spallek, Ingelheim (DE); Johannes Geser, Gerlingen (DE)

(73) Assignee: KOCHER-PLASTIK MASCHINENBAU GMBH, Sulzbach-Laufen (DE)

( * ) Notice: Subject to any disclaimer, the term of this patent is extended or adjusted under 35 U.S.C. 154(b) by 659 days.

(21) Appl. No.: 14/783,542

(22) PCT Filed: Feb. 15, 2014

(86) PCT No.: PCT/EP2014/000421
§ 371 (c)(1),
(2) Date: Oct. 9, 2015

(87) PCT Pub. No.: WO2014/169979
PCT Pub. Date: Oct. 23, 2014

(65) Prior Publication Data
US 2016/0060006 A1    Mar. 3, 2016

(30) Foreign Application Priority Data

Apr. 19, 2013  (DE) ........................ 10 2013 007 063

(51) Int. Cl.
*B65D 51/24* (2006.01)
*A61F 9/00* (2006.01)
(Continued)

(52) U.S. Cl.
CPC .......... *B65D 51/243* (2013.01); *A61F 9/0008* (2013.01); *B65D 39/0052* (2013.01);
(Continued)

(58) Field of Classification Search
CPC .......... B65D 2101/0038; B65D 51/225; B65D 51/243; B65D 2101/0053
See application file for complete search history.

(56) References Cited

U.S. PATENT DOCUMENTS

| 5,975,369 A | 11/1999 | Yurkewicz et al. |
| 6,321,924 B1 | 11/2001 | Yurkewicz et al. |
| (Continued) | | |

FOREIGN PATENT DOCUMENTS

| DE | 10 2005 025 760 | 12/2006 |
| WO | 86/03126 | 6/1986 |
| (Continued) | | |

OTHER PUBLICATIONS

International Search Report (ISR) dated Apr. 8, 2014 in International (PCT) Application No. PCT/EP2014/000421.

*Primary Examiner* — Andrew T Kirsch
*Assistant Examiner* — Don M Anderson
(74) *Attorney, Agent, or Firm* — Wenderoth, Lind & Ponack, L.L.P.

(57) ABSTRACT

A container, in particular a plastic vial produced in the blow-molding method and filled and closed in the mold, has a neck part (5) joined to a container body (1). The neck part receives a one-part or multi-part cap (2). A fixing part (29) is connected to the cap (2) by a breaking point (31), which can be detached by a relative rotational motion between the cap (2) and the container body (1). Each breaking point (31) can be detached by rotational motions in both rotational directions with approximately the same angle of rotation and approximately the same torque.

15 Claims, 6 Drawing Sheets

(51) Int. Cl.
*B65D 51/22* (2006.01)
*B65D 39/00* (2006.01)
*B65D 41/58* (2006.01)

(52) U.S. Cl.
CPC ........... *B65D 41/58* (2013.01); *B65D 51/225* (2013.01); *B65D 51/227* (2013.01); *B65D 2101/0038* (2013.01); *B65D 2251/0015* (2013.01); *B65D 2251/0028* (2013.01); *B65D 2251/0056* (2013.01); *B65D 2251/0096* (2013.01)

(56) References Cited

U.S. PATENT DOCUMENTS

| | | |
|---|---|---|
| 2003/0187403 A1 | 10/2003 | Balestracci |
| 2003/0230546 A1 | 12/2003 | Yurkewicz et al. |
| 2004/0200855 A1 | 10/2004 | Weiler |
| 2004/0225258 A1 | 11/2004 | Balestracci |
| 2008/0073348 A1* | 3/2008 | Pritikin ................ B65D 47/142 220/278 |
| 2009/0230080 A1 | 9/2009 | Hansen |

FOREIGN PATENT DOCUMENTS

| | | |
|---|---|---|
| WO | 98/55368 | 12/1998 |
| WO | 00/50108 | 8/2000 |
| WO | 2012/113008 | 8/2012 |

* cited by examiner

CONTAINER

FIELD OF THE INVENTION

The invention relates to a container, in particular a plastic vial produced in the blow-molding method and filled and closed in the mold. The container comprises a neck part adjoining a container body. A one-part or multi-part cap can be placed in the neck part, in particular slipped into it. A fixing part is allocated to the cap and is connected to the cap by at least one predetermined breaking point. The predetermined breaking point can be detached by a relative rotational motion between the cap and the container body or parts thereof.

BACKGROUND OF THE INVENTION

DE 42 32 305 C1 discloses a multi-part cap for containers, in particular bottles produced in the blow-molding method and filled and closed in the mold, including in the form of a vial. The container has a neck part, onto which the cap can be placed. Adjoining to the section receiving the neck part, the cap has an integrally formed part that is formed as a dropper. This patent describes, as further known solutions, bottles of this kind having an externally threaded neck that is closed at its free end by a closure part, integrally formed with the neck part. A cap screwed onto the neck part is provided with a centrally arranged spike on the inside as an opening device with which the closure part can be pierced. When the cap is removed after piercing the closure part, the liquid present in the bottle can be discharged through the opening created in the closure part.

DE 195 80 104 T1 discloses a container solution having a hermetically sealed container which is provided with a covering cap. A spike incorporated in the cap serves for piercing a membrane on the neck part of the container. The hollow spike forms an attachment that defines a discharge path in a manner that ensures a controlled removal of liquid. To this end, the spike, acting as an opening device, pierces the membrane. After removal of a first cap part, the spike is retained in the membrane by the second cap part to provide a controlled dispenser or discharge opening for the container. The first cap part can then serve again for closing the dispenser or discharge opening for the container body of the container.

A container is disclosed in U.S. Pat. No. 5,954,233. For an opening process of the container, in addition to a ramp guide between ramp parts of a first cap part and a second cap part that, when actuated, effects a longitudinal insertion of the second cap part into a locked position on the neck part of the container, which is accompanied by a corresponding exertion of force during actuation, is also provided with nose-shaped projecting engaging parts on the neck part. The engaging parts engage with associated recesses of the second cap part for its non-rotatable fixing on the neck part, allowing an opening process of the container in both possible directions of rotation of the first cap part during its screw-on or unscrewing process onto the, or from the, container, respectively. Comparable solutions, however with only one cap part or one cap, have at its end facing the container body a piercing spike, which, as an opening device. The piercing spike pierces a sealing membrane or housing cover part facing it, when screwing the cap onto or off a corresponding threaded segment of the neck part of the container body, as disclosed in U.S. Pat. No. 3,454,196 A1 as well as U.S. Pat. No. 4,723,687 A1.

All solutions in the prior art mentioned above have in common that they do not have a tamper-evident closure, which is an important feature for pertinent containers. A tamper-evident closure clearly indicates to the user possible tampering with the opening-closing system, which is undesirable, or even preventing such tampering.

On the other hand, a container with a two-part cap solution is disclosed in DE 10 2005 025 760 A1. The container body is provided with a tamper-evident closure. This container body can in turn be manufactured in a simple and cost-effective manner by a blow-molding, filling, and closing method, as it has become known under the trademark "Bottelpack®" in the trade. The cap parts, as well as the tamper-evident closure, can be produced preferably by injection molding. Especially, when such containers are provided for containing a sensitive filling material, such as food or, in particular, pharmaceutical or cosmetic substances, the fixing parts that, during first use of the container, need to be separated from the first cap part by releasing associated predetermined breaking points to perform the opening process. The fixing parts have a particularly important function as a tamper-evident closure by clearly indicating, or even preventing, tampering with the opening-closing system as outlined above. For this purpose, the fixing part is connected with the edge of its associated first cap part in the form of a retaining ring via predetermined breaking points in the aforementioned known container.

The fixing part is mounted on the neck part of the container body and is rotatable in the screwing-on direction, but is fixed against rotation in the unscrewing direction by a unidirectional locking mechanism. To break the tamper-evident closure, i.e., release the connection with first cap part, the user must continue turning the initially loose first cap part in the screwing direction (down) until the retaining ring makes contact with the container shoulder, causing an axial compression between the shoulder, retaining ring and cap part and the predetermined breaking points are torn during further rotation by superimposed axial and torsional forces.

When the user starts, on the other hand, with a rotation in screw-off direction for the first opening, a completely different type of release behavior arises compared to the long paths (up to several rotations) required with the former approach (screwing in). Since the rotation of the locking ring in the unscrewing direction is blocked, releasing the predetermined breaking points is carried out without pronounced deformation and over a short path (small angle of rotation). In this case, however, the user must reverse the direction of rotation after releasing the predetermined breaking points to perform the piercing process, and thus the opening of the container body, by unscrewing the first cap part and driving the second cap part with the spike cannula located thereon.

SUMMARY OF THE INVENTION

An object of the invention is to provide an improved container of the type under consideration that, while maintaining the advantages achieved in the prior art, is characterized by improved ease of operation.

According to the invention, this object is basically achieved by a container having, as an essential feature of the invention, a respective predetermined breaking point that can be released by a rotational movement in either rotational direction and with approximately the same rotation angle and torque. Due to the fact that the tearing off of the tamper-evident closure is carried out with a small angle of rotation, i.e., over a short path, even if the user begins the opening cycle with a rotational movement in the unscrewing direction, there is no superposition of the torque required for the release of the breaking points with other torques, such as by piercing the spike cannula, as is sometimes the case with known solutions. That is the case, where, during the unscrewing process, the second cap part is driven to make contact with or engage with the neck part, and the piercing of the spike cannula occurs before the release process takes place by the fixing ring making contact with the container shoulder. In the invention, in contrast, the processes of piercing by the spike cannula or the engaging of the cap, or of the respective cap part, takes place independently of the breaking the tamper-evident closure. Specifically, the release of the predetermined breaking points is carried out with the invention for both directions of rotation, with approximately the same torque and angle of rotation.

In a preferred embodiment of the container according to the invention, the respective predetermined breaking point is implemented using a web bridge with a preferably small cross section. The web bridge extends between the cap and the fixing part. By reducing the respective predetermined breaking point to a punctiform separating point, the respective predetermined breaking point can be released with relatively low actuating forces. Nevertheless, in the sense of an effective tamper-evident closure, the cap or the respective cap part cannot be unintentionally released for an opening process. Accordingly, an effective lock is added against unwanted or unintended actuation.

In another preferred embodiment of the container according to the invention, the opening device opens the container body by piercing, cutting, or by tearing or cutting off at least parts of the container body. Alternatively, an existing opening in the container body is sealed in a removable manner by a closure body, such as a sealing film that can also be formed to be penetrable. The sealing film is pierced, for example, by an opening device formed as a piercing spike.

If the container is equipped with a one-piece cap or simply with a single cap part, a piercing spike may be present on the inside of the cap or of the cap part. The piercing spike pierces open the container body during the screwing-on process for a removal process of the container contents. In alternative embodiments, the cap or the respective cap part has a cutting or tearing ring that serves as an opening device for opening the container body.

In a particularly preferred embodiment of the container according to the invention, the cap has at least a first cap part and a second cap part. The second cap part at least partially extends between the first cap part and the neck part and is provided with at an opening device having at least one opening for opening the container body. The opening is closable by the first cap part. By the attachment or unscrewing process of the first cap part, the first cap part drives the second cap part such that the opening device causes the opening of the container body.

Depending on the particular application and depending on customer requirements, two different opening variations can be implemented in this manner with only one container. A first option is to deliver the preferred formed container with an open cap assembly, i.e., the first cap part is only partially screwed onto the associated thread of the container body, for example, half a turn. The user then must first continue rotating the first cap part further down along the thread to open the container body in a regular manner by the opening device in the shape of a spike. The second cap part remains on the neck part. The upper cap, in the form of the first cap part, must be rotated in the direction opposite to the previous screw-on direction to release the opening for removal of the stored medium from the container.

In a second option, the container can be delivered already open, i.e., the first cap part is completely screwed on. The second cap part is set fixed on the neck part, and the opening device, for example in the form of a piercing spike, has already pierced through the opening in the container body for releasing the same. The user of the container must now only unscrew or untwist the upper first cap part to use the container contents, for example, in the form of eye drops contained therein. Accordingly, with only one assembly, two different customer-specific types of removal options can realized, each of them secured by the described tamper-evident closure. Where screwing or unscrewing processes of the respective cap or the respective cap part are concerned, this process includes re-releasable engaging processes and engagements between said parts of container.

In exemplary embodiments in which the fixing part, serving as a tamper-evident closure, is in the form of a ring surrounding the neck part in the assembled state, a stop device can be formed on the inside of the ring. The outside of the neck part blocks a relative rotation in both directions of rotation.

In advantageous exemplary embodiments, the stop device has at least one wing part, preferably a plurality of wing parts, radially projecting from the inside of the ring. The wing parts act together with blocking elements on the neck part, preventing rotations in both directions of rotation. A tamper-evident ring to tear off of the cap at the respective predetermined breaking points in both directions of rotation in a similar and essentially brittle manner, materials with low tensile strength and a high elasticity modulus are particularly suitable, such as styrene acrylonitrile (SAN), polystyrene (PS), polyethylene terephthalate (PET) polyamide (PA), high density polyethylene (HDPE), polypropylene (PP), and the like.

The wing parts can be provided in the form of ledges extending axially on the inside of the ring. The ledges act together with associated radially projecting blocking elements on the neck part. The ledges may have a rectangular cross-section.

Alternatively, ledges with a T-shaped, Y-shaped or V-shaped cross-section are provided.

The stop device can also be formed in such a way that, on a respective wing part of the ring, a groove is provided for the engagement with an associated blocking element on the neck part.

The number of blocking elements and the wing parts may be between one and twelve. Preferably, two to four blocking elements and four to eight wing parts are provided.

In especially advantageous embodiments, the ring serving as a tamper-evident closure has the shape of a crown with a rim of perforations, which perforations are open on the edge facing the first cap part. Due to the perforations, the crown shape allows the user an additional, simple visual inspection of whether the first cap part is sufficiently screwed in to perform the piercing process by driving the second cap part.

The object of the invention is also achieved according to another aspect of the invention by a container having a second cap part, remaining on the neck part when the container body is open. The second cap part is resiliently expandable in its bell part, extending over the end area of the neck part. This structure allows for the process, of screwing and of opening by driving the second cap part, to be performed with little need for torque. Due to the resilience of its bell part, the second cap part can be placed securely on the end area of the neck part without great need for force.

To provide the desired resilience, axial slots may be formed in the bell part, extending from the edge of the opening.

Advantageously, an engaging connection between the second cap part and the neck part can be provided. The ribs extend circumferentially on the inside of the bell part for engaging in an annular groove on the neck part.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure.

DETAILED DESCRIPTION OF THE INVENTION

Figure 1:
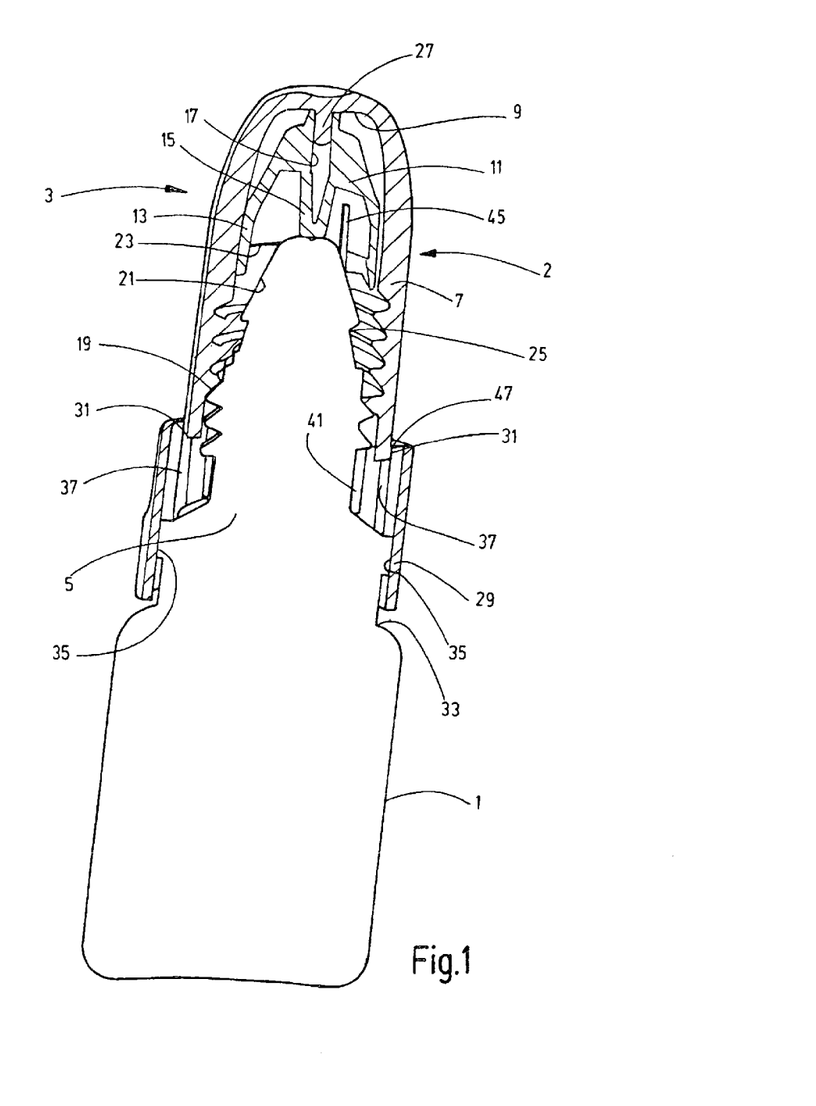
FIG. 1 is a side view in section of a container with a two-piece cap, with the container body shown only schematically in simplified form, showing only its outline according to a first exemplary embodiment of the invention.
Figure 2:
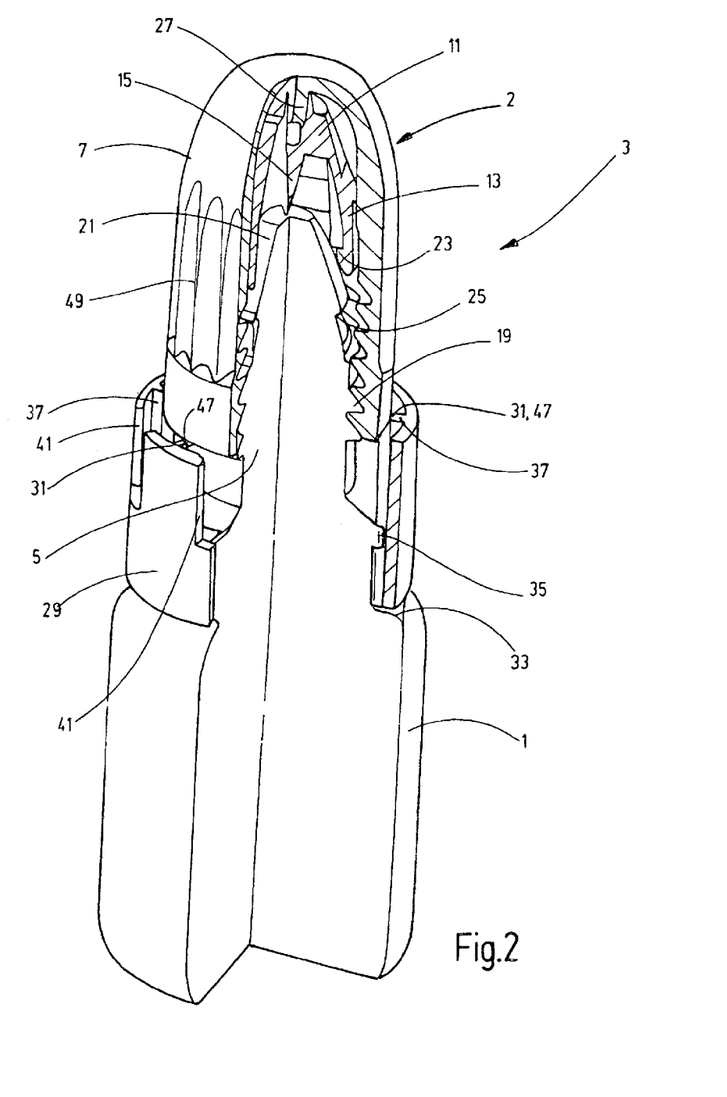
FIG. 2 is a perspective view in section of the first exemplary embodiment, wherein the central area is shown in the manner of an angle cut.
Figure 3:
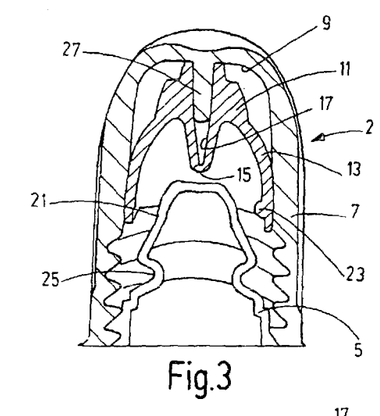
FIG. 3 is a partial side view in section of only the upper end portion of the neck part of the container body, with attached first and second cap part of the complete cap of the first exemplary embodiment.
Figure 4:
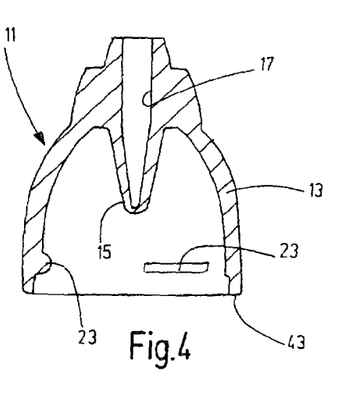
FIG. 4 is an enlarged side view in section of only the second cap part of FIG. 3.
Figure 5:
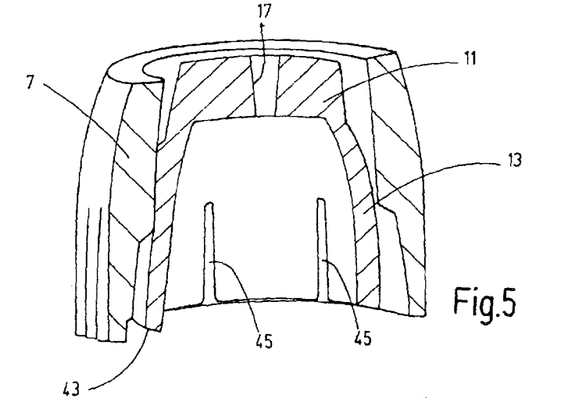
FIG. 5 is a further enlarged side view, partially in section, of only the upper portion of the first and second cap parts of FIG. 3.
Figure 6:
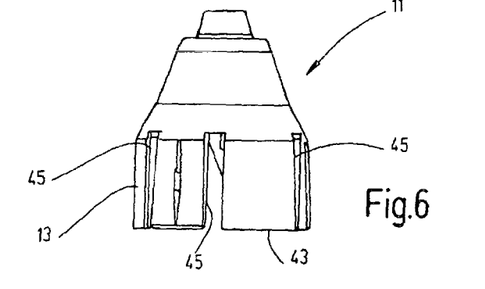
FIG. 6 is a side view of the second cap part, shown separately, of FIG. 3.
Figure 7:
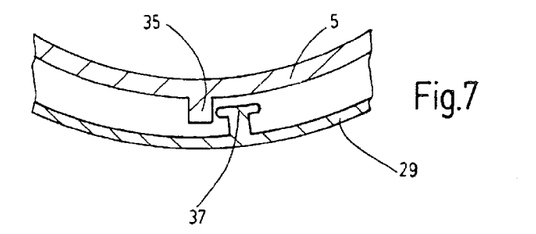
FIG. 7 is an enlarged, partial plan view in section of a peripheral region of the neck part with a protruding blocking element and the annular fixing part, serving as a tamper-evident closure, with radially inwardly protruding wing part, having a T-shaped cross section.
Figure 8:
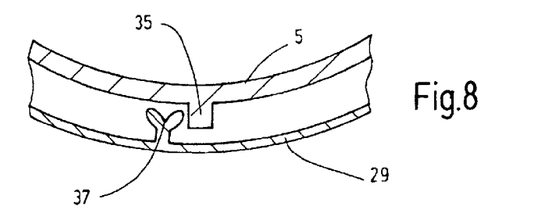
FIGS. 8 and 9 are enlarged, partial plan views in section of the neck part with Y-shaped and V-shaped wing part, respectively.
Figure 9:
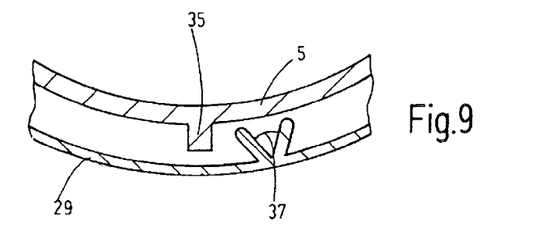

FIGS. 1 and 2 show a first exemplary embodiment of a container according to the invention. As indicated there, the container includes a container body 1, with a two-part cap 2 and an opening device 3. The container body 1 is formed in the manner of a vial made of a plastic material, in which a fluid, not shown in further detail, can be stored, for example, a medically effective liquid, such as in the form of eye drops or the like. Other types of media, including, for example, gaseous or paste-like substances, can be introduced into the container body 1, for example by the above-mentioned blow molding process, which has become known in the trade under the trademark "Bottelpack®." The opening device 3 can also be used for container bodies produced in a different manner.

Adjoining the top of the container body 1 is a neck part 5, onto which a first cap part 7 of the cap 2 can be screwed. A second cap part 11 of the cap 2 is inserted in the first cap part 7 at its closed upper end 9, for which FIGS. 3 to 6 illustrate further details. The second cap part 11 is shown separately in FIG. 4 in a longitudinal section, and in a side view in FIG. 6. The second cap part 11 is provided as an opening element for the container body 1. On its side facing the neck part 5, second cap part 11 is provided with a bell portion 13. In the center of bell portion 13, a spike cannula 15 is formed. The cannula 15 continues to the upper end of the second cap part 11 via a channel 17. When screwing the first cap part 7 onto the thread 19 of the neck part 5, the second cap part 11 is driven by the closed end 9 of the first cap part 7 so that the bell part 13 is pushed onto the cone-shaped end part 21 of the neck part 5. The spike cannula 15 pierces the wall of the container body 1 to form an opening for dispensing of the container contents via the channel 17. During this opening process, the spike cannula 15 is pierced open at its lower end for fluid removal under formation of a channel opening, or it has already had corresponding fluid passages to respective discharge openings into the channel 17 from the outset.

FIGS. 1 and 2 show the state before first opening. The first cap part 7 initially is only loosely fitted to the neck part 5. The cap part 7 is snapped onto the neck part 5 during the assembly process, without rotational movement by axially sliding it onto the upper end of the thread 19. As shown in FIGS. 1 and 2, the thread 19 has a saw-tooth shape, which allows for this engagement, while securing the cap part 7 against axial movement away from the neck part 5. When, for the first opening process, the cap part 7 is screwed on and the spike cannula 15 performs the puncture, the second cap part 11 is placed onto the cone-shaped end part 21 of the neck part 5 with its bell part 13. To rest on the end part 21, the bell part 13 has a plurality of projecting ribs 23 on the inside of the bell part, extending in circumferential direction. As seen in particular FIGS. 3 and 4, ribs 23 engage with an annular groove 25 on end part 21. For an open container body 1 and a screwed on first cap part 7, the channel 17 is closed by a pin 27 forming a stopper, which is formed at the end 9 of the cap part 7.

For the formation of a tamper-evident closure that provides an indication of whether the container is still in its original state or manipulation of the opening device 3 has already occurred, a fixing part in the form of a ring 29 is allocated to the first cap part 7. The ring 29, in the assembled state or original state, is integrally formed on the opening edge of the first cap part 7 via predetermined breaking points 31. The release of this connection by breaking the predetermined breaking points 31 is performed by rotating the cap part 7 relative to the ring 29. To allow for the relative rotation, a stop device is provided between the ring 29 and the neck part 5 of the container body 1, which stop device secures the ring 29 against rotation in both directions of rotation. As shown in FIGS. 1 and 2, the ring 29 surrounds the neck part 5 in the area adjoining the container shoulder 33. In the embodiment illustrated in FIGS. 1 and 2, the stop device is provided with blocking elements 35 radially projecting on the neck part 5. Blocking elements 35 act together with the wing parts projecting radially inwardly from the inside of the ring 29 to form locks against rotation. In the embodiment of FIGS. 1 and 2, the wing parts are formed by ledges 37 that have quadrilateral cross sections and extend in the axial direction along the inside of the ring 29. While in FIGS. 1 and 2 only a few blocking elements 35 and ledges 37 are visible, a plurality of blocking elements 35 and ledges 37 are present to form an effective barrier even at small angles of rotation in both directions of rotation. Preferably two to four blocking elements 35 and four to eight wing parts are provided, for example in the form of ledges 37.

Figure 10:
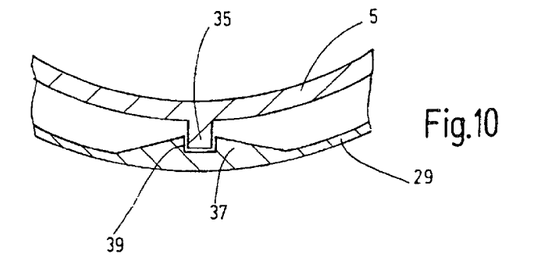
FIG. 10 is an enlarged, partial plan view in section of an axial groove located on the respective wing part of the annular fixing part for the engagement of an associated blocking element on the neck part.

FIGS. 7 to 10 illustrate modified embodiments with a modified design of the stop device. The examples of FIGS. 7 to 9 differ with respect to the exemplary embodiment of FIGS. 1 and 2 in that ledges 37 with modified cross-sectional shapes are provided, namely T-shaped ledges 37 in FIG. 7, Y-shaped ledges 37 in FIG. 8, and V-shaped ledges 37 in FIG. 9. By the cross-sectional shape extending further circumferentially, the respective dead space between successive blocking elements 35 is reduced, so that the blocking is effective even for small angles of rotation in both directions of rotation. The example of FIG. 10 shows wing parts 37 on the ring 29 with an axially extending groove 39 for the engagement with a respective blocking element 35. In this example, the free angle of rotation is limited to virtually zero. Alternatively, the individual blocking elements 35 can be at least partially disposed on the ring 29, and the interacting elements or ledges 37 can be disposed on the container body 1.

Due to the blocking of the relative rotation in both directions of rotation, the user can release the tamper-evident closure by turning the cap part 7 in any direction without having to perform several revolutions. With the tamper-evident closure released, the user is free to perform the piercing and opening process by further screwing on, and then remove the first cap part 7 to dispense contents. The second cap part 11 is pushed onto the end part 21 of the neck part 5 and remains engaged. After dispensing the contents, a closing process may be performed again by the pin 27 by screwing the first cap part 7 on.

In the embodiment shown in FIGS. 1 and 2 the ring 29 forming the tamper-evident closure has the shape of a crown with a rim of perforations 41, which are open on the upper edge facing the first cap part 7. These perforations 41 allow the user a simple visual inspection if the cap parts 7, 11 are screwed on sufficiently for the piercing and opening process.

To make placing the second cap part 11 onto the end part 21 of the neck part 5 and the securing by engaging the bell part 13 simple and secure, several slots 45, beginning at the opening edge 43 and extending axially, are formed in the bell part 13. They provide the bell portion 13 with a certain elastic resilience, so that the bell part 13 can expand radially when pushed onto the end part 21 before the ribs 23 cause the engagement of the second cap part 11 with the neck part 5 by snapping into the groove 25.

The ledges 37 extend in vertical direction in the perspective of FIGS. 1 and 2 over the entire inner circumference of the ring 29 from top to bottom for secure anchoring and force-transmission. At the upper transition point, the ledges 37 are then connected with the outer cap 7 only via small web bridges 47 at their lower ends. Despite the large number of predetermined breaking points 31 formed via the web bridges 47, which are released collectively, only low actuation forces are necessary for releasing the cap 7 from the ring 29. The web bridges, which are moreover thin-walled, provide the connection between the lower circumferential edge of the respective outer cap 2 to the edge-like longitudinal ridges 37 virtually without spacing. Predetermined breaking points 31 are also provided via the above mentioned web bridges 47 in a number comparable to the number of ledges 37. Predetermined breaking point solutions are here also possible in which, if appropriate, the respective inner side of the ledge 37 is connected to the facing outer side of cap 2 in a releasable manner over a longer distance. In particular, seen in the perspective of the individual figures, the respective web bridge 47 has a horizontal orientation with respect to the vertically arranged ledges 37.

Figure 11:
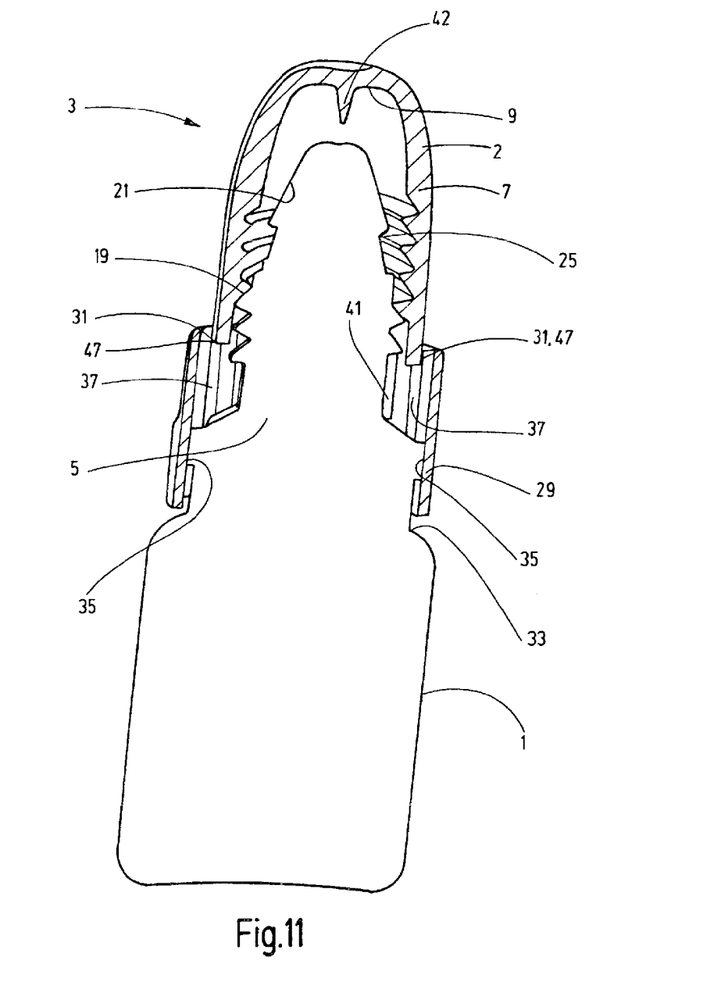
FIG. 11 is a side view in section of a container with only one cap part according to a second exemplary embodiment of the invention.

The second embodiment according to the illustration of FIG. 11 is constructed similarly to the solution according to FIG. 1 with respect to the graphic representation. Instead of a two-part cap, only a one-part cap 2 is used. A piercing spike 42, is a solid form 42 and provides for the opening of the container body 1 at its upper side in the region of the neck part 5, when the cap 2 is moved downward over the thread sections 19 that can be allocated thereto by a screwing-in. In this case as well, the tamper-evident closure must first be released via the predetermined breaking points 31, 47. If the cap 2 is removed from the container body 1 after piercing the container body 1 by the solid spike 42, a removal process can take place for the container contents through the opening (not shown) formed in the neck part 5. Analogous embodiments to the design of FIG. 11 are obtained by the use of other one-piece caps, which can open the container body not by piercing or cutting in, but by tearing or cutting off. In such relevant cases as well, for the purposes of the invention, only a retaining ring 29 attached via the predetermined breaking points 31 is provided as a tamper-evident closure.

Figure 12A:
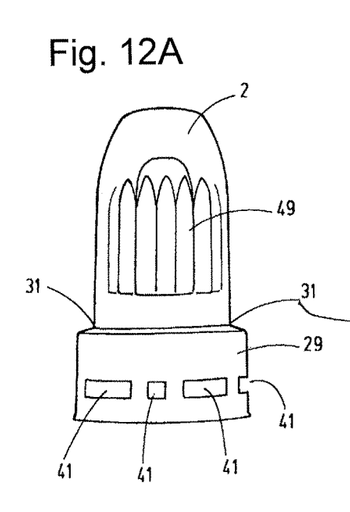
FIGS. 12A-D are side views of four different variants of annular fixing parts with differently designed window openings of the container of FIG. 11.
Figure 12B:
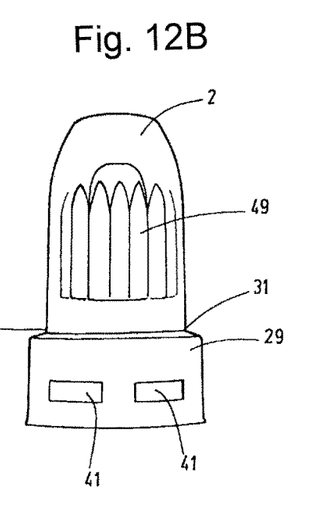

In the embodiments according to FIGS. 1 to 11, the retaining ring 29 is provided with slot-shaped perforations in the form of a crown at its upper side in perspective of the figures. The representation of FIGS. 12A-D, on the other hand, shows other embodiments of perforations 41 for the ring 29. In FIG. 12A, the ring 29 is provided with slot-shaped perforations 41 in a horizontal orientation. The linear extension of perforations 41 may be chosen differently, allowing for a division into groups of different lengths. In contrast, in the embodiment in FIG. 12B, the horizontally arranged perforations 41 extend over the entire outer circumference of ring 29 and are formed with the same length.

Figure 12C:
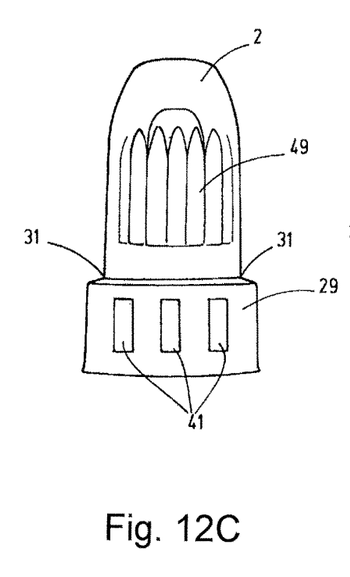
Figure 12D:
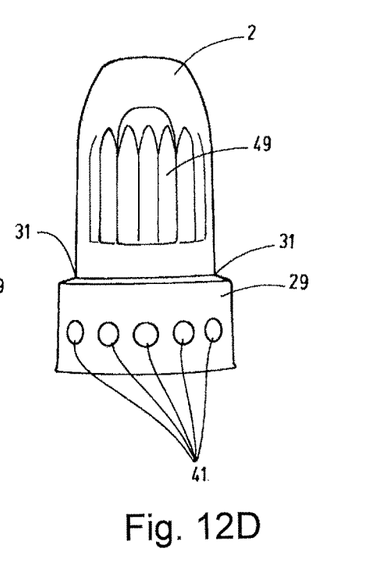

The embodiment according to FIG. 12C perforations 41 are in vertical orientations at an equal distance from each other. The pertinent vertical slits are bounded on their outer circumference by the material of the ring 29. FIG. 12D shows perforations in the ring 29 in a circular ring shape. In this case, other configurations of any kind are possible, including in a polygonal shape. Ultimately, the perforations 41 in the manner of window openings are to provide the operator with visual feedback from outside as to what extent the cap 2 is screwed in the direction of the ring 29 by the lower outer periphery of the cap 2. When being screwed in, overlapping of cap 2 with the respective passage point 41 allows for visual determination of the position detection for the cap 2. Due to the fact that the openings 41 are arranged at several locations along the outer periphery of the ring 29, the desired visual detection can be performed regardless of the location position of the container 1 with respect to the user. For a better actuation of the respective cap 2, it may be provided with ribbing 49 on is outer peripheral side.

While various embodiments have been chosen to illustrate the invention, it will be understood by those skilled in the art that various changes and modifications can be made therein without departing from the scope of the invention as defined in the claims.

The invention claimed is:

1. A container, comprising:
   a container body having a hollow interior for contents;
   a neck part joined to said container body;
   a cap mounted axially on said neck part;
   a fixing part being connected to said cap by predetermined breaking points and being detachable by relative rotation between said cap and said container body, in both of opposite first and second rotational directions, said fixing part including a tamper-evident closure ring surrounding said neck part in an assembled state thereof; and
   ledges extending axially and radially on an inside surface of said ring and blocking elements extending radially on an outside surface of said neck part, said ledges and blocking elements blocking rotation of said ring relative to said neck part in both of the first and second rotational directions, said predetermined breaking points being web bridges directly connecting only said ledges to a lower end of said cap.

2. A container according to claim 1 wherein
   said cap comprises an opening device penetrating said neck part to produce an opening therein for dispersing the contents in said container body.

3. A container according to claim 2 wherein
   said opening device comprises a piercing spike.

4. A container according to claim 2 wherein
   said cap consists of one unitary piece of plastic.

5. A container according to claim 1 wherein
   said ledges have rectangular cross sections.

6. A container according to claim 1 wherein
   said ledges have at least one of T-shaped, Y-shaped or V-shaped cross sections.

7. A container according to claim 1 wherein
   said ledges comprise grooves opening toward said neck part and receiving said blocking elements.

8. A container according to claim 1 wherein
   a number of said blocking elements and a number of said ledges are at least two and not greater than twelve.

9. A container according to claim 1 wherein
   a number of said blocking elements is at least two and not greater than four; and
   the number of said ledges is at last four and is not greater than eight.

10. A container according to claim 1 wherein
    said ring is crown-shaped and comprises a rim of perforations open on an edge of said ring facing said cap.

11. A container according to claim 1 wherein
    said ring comprises a window-shaped perforation with at least one of a slot shape, a round shape or a polygonal shape.

12. A container according to claim 1 wherein
    said cap is threaded on said neck part.

13. A container according to claim 1 wherein
    said ring is radially wider than said cap.

14. A container according to claim 13 wherein
    said web bridges extend radially between said ledges and said cap.

15. A container according to claim 1 wherein
    said cap comprises a first cap part and a second cap part, said second cap part extending between said first cap part and said neck part and having an opening device with an opening for opening said container body, said opening in said opening device being releasably closable by said first cap part; and
    said first cap part threadedly engages said neck part to drive said second part such that said opening device is driven into said neck part to form an opening in said container allowing dispensing of the contents in said container body when said first cap part is removed from said neck part.

* * * * *